United States Patent
Feldman et al.

[11] Patent Number: 5,634,880
[45] Date of Patent: Jun. 3, 1997

[54] ENDOSCOPE PRESSURE EQUALIZATION SYSTEM AND METHOD

[75] Inventors: Leslie A. Feldman, Calabasas Hills; Henry Hui, Laguna Niguel, both of Calif.; Reinhard Kowatsch, Hamburg, Germany; Tsutomu Hayashida, Saitama, Japan; Michael Hahs, San Clemente; Charles Howlett, Laguna Beach, both of Calif.

[73] Assignee: Johnson & Johnson Medical, Inc., Arlington, Tex.

[21] Appl. No.: 446,377

[22] Filed: May 22, 1995

[51] Int. Cl.⁶ .................................................. A61B 1/012
[52] U.S. Cl. ..................... 600/132; 600/133; 600/159
[58] Field of Search ........................... 600/133, 132, 600/153, 155, 156, 159; 137/541, 550

[56] References Cited

U.S. PATENT DOCUMENTS

| | | |
|---|---|---|
| 3,835,884 | 9/1974 | Ishikawa et al. ............ 137/550 |
| 4,129,145 | 12/1978 | Wynn . |
| 4,254,624 | 3/1981 | Komiya . |
| 4,309,992 | 1/1982 | Dodak et al. ............ 604/19 |
| 4,329,980 | 5/1982 | Terada . |
| 4,363,322 | 12/1982 | Andersson . |
| 4,506,544 | 3/1985 | Shimizu . |
| 4,527,551 | 7/1985 | Ishii . |
| 4,537,209 | 8/1985 | Sasa . |
| 4,538,593 | 9/1985 | Ishii . |
| 4,545,369 | 10/1985 | Sato . |
| 4,643,876 | 2/1987 | Jacobs et al. . |
| 4,706,654 | 11/1987 | Ogiu et al. . |
| 4,716,025 | 12/1987 | Nichols . |
| 4,805,595 | 2/1989 | Kanbara . |
| 4,878,484 | 11/1989 | Miyagi . |
| 5,059,167 | 10/1991 | Lundquist et al. ............ 600/17 |
| 5,343,854 | 9/1994 | Katsurada . |
| 5,433,801 | 7/1995 | Langford . |
| 5,508,009 | 4/1996 | Rickloff et al. . |

FOREIGN PATENT DOCUMENTS 5253168  10/1968  Japan .

OTHER PUBLICATIONS

Olympus, Operating Instructions Olympus BF Type P30, Date Unknown.

*Primary Examiner*—Richard J. Apley
*Assistant Examiner*—David R. Risley
*Attorney, Agent, or Firm*—Andrew C. Farmer

[57] ABSTRACT

A pressure equalization device connects to a port on an endoscope and equalizes the pressure within the endoscope to an environment thereabout. An outlet check valve allows flow out of the port and blocks flow into the port. A filter may be provided for preventing known chemical agents from entering the port. If the agent is hydrogen peroxide, the filter preferably comprises a catalyst, such as copper wool, for decomposing the hydrogen peroxide into water and oxygen. An inlet check valve may also be provided to communicate with the endoscope port and allow flow into the port in response to a downstream pressure gradient exceeding a predetermined value.

18 Claims, 2 Drawing Sheets

ENDOSCOPE PRESSURE EQUALIZATION SYSTEM AND METHOD

BACKGROUND OF THE INVENTION

Field of the Invention

The present invention relates to a system and method for equalizing pressure between an interior space in an endoscope and an environment about the endoscope.

BACKGROUND INFORMATION

A typical endoscope comprises an elongated tube suitable for introduction into a human or animal body. A lens at a distal tip of the endoscope forms an image of an internal area of the body. Means such as fiber optic cables or video transmission transmit the image the length of the endoscope to a point outside of the body where it can be viewed by a surgeon or other user of the endoscope. Of course, endoscopes are not limited to medical uses, and are also useful in machine diagnostics and repair among other uses. Regardless of its intended use, a flexible distal portion allows the endoscope to negotiate non-linear passages.

In addition to the image transmission means, the distal portion of the endoscope typically contains one or more tubular passages for passing air, liquid, or instruments. Flexible endoscopes usually also contain one or more wires for controlling movement of the tip of the endoscope. A flexible sheath surrounds the flexible portion of the endoscope to protect it from its environment and to protect the body or other environment from the internal parts of the endoscope.

For reasons of sanitation endoscopes are typically washed and sterilized after each use. For added convenience during these procedures, many endoscopes are provided with an entirely water tight structure to protect the internal components of the endoscope from washing and sterilization agents. In a flexible endoscope, the flexible elastomeric sheath surrounding the flexible portion of the endoscope forms an integral part of this water tight structure.

Traditional methods of sterilization, such as high pressure steam, may damage the delicate internal workings and the flexible sheath of an endoscope. The latest sterilization equipment subjects the endoscope to an antimicrobial gas such as hydrogen peroxide or ethylene oxide, perhaps in combination with a plasma field. These sterilizers typically maintain the endoscope in a reduced pressure environment during the sterilization procedure.

A significant area of unused space occupies the flexible portion of most endoscopes. Of course, this space is filled with gas, typically air. As the pressure is reduced, the gas trapped inside of the endoscope exerts tremendous pressure against the elastomeric sheath. If this pressure is not released, the sheath could rupture. In general rigid endoscopes easily withstand a one atmosphere pressure exerted by entrapped gases; however, even rigid endoscopes may be constructed with delicate components that are sensitive to pressure within the endoscope.

At least one manufacturer provides an endoscope with a sealable port leading into the interior of the endoscope. During sterilization in a reduced pressure environment the port may be opened to allow the interior of the endoscope to communicate with the sterilization atmosphere and thus relieve the excess pressure within the endoscope. The port is also used to check for leaks in the endoscope, especially in the sheath, through the controlled application of gas pressure to the endoscope's interior while it is submerged in water.

For convenience, at least one manufacturer supplies an apertured cap which may be fitted over the port during sterilization which opens a valve within the port and thus places the interior of the endoscope into communication with the atmosphere during the sterilization procedure. While this simple device protects the elastomeric sheath from bursting, it also allows the gaseous antimicrobial agent to enter the interior of the endoscope. Presence of this agent within the endoscope is not necessarily desirable. This portion of the endoscope does not come into contact with the patient so does not require sterilization. Further, the agent could possibly harm the interior of the endoscope. Generally, the port should be left open for a sufficient amount of time after the sterilization procedure for the agent to disperse from the interior of the endoscope. Of course, this may increase the length of time required to complete the sterilization procedure.

SUMMARY OF THE INVENTION

The present invention overcomes these and other limitations in the prior art by providing a device and method for equalizing the pressure within an endoscope during a sterilization procedure white inhibiting the antimicrobial gas from entering the interior of the endoscope.

A pressure equalization device according to the present invention equalizes the pressure within an endoscope with an environment thereabout. The device connects to a port on the endoscope which in turn leads to the internal space from the environment. An outlet check valve communicates with the endoscope port and allows flow out of the port while inhibiting flow into the port. Thus, when the endoscope is subjected to a reduced pressure in the environment, gas within the endoscope interior space escapes to the environment through the outlet check valve to relieve pressure within the interior space. After the pressure in the interior space is equalized with the pressure in the environment, the outlet check valve inhibits reverse flow therethrough of gas from the environment into the interior space.

Preferably, the filter in the outlet flow path prevents hydrogen peroxide from entering the port. Thus, when the device is employed during a reduced pressure hydrogen peroxide sterilization procedure, hydrogen peroxide which may happen to leak past the outlet check valve towards the port is filtered by the filter. The filter may comprise a catalyst, such as copper wool, for decomposing hydrogen peroxide to water and oxygen.

Preferably, an inlet check valve means also communicates with the endoscope port to allow flow into the port in response to a downstream pressure gradient exceeding a predetermined value, preferably in the range of 1.5 to 5 pounds per square inch. Positive closure means on the outlet check valve may be provided to inhibit flow therethrough except in response to a downstream pressure gradient exceeding a predetermined value, also preferably 1.5 to 5 pounds per square inch.

The port on such endoscopes often have an internal valve and the device of the present invention is preferably provided with an opening means for opening the port's internal valve. To enhance operator compliance, the device may be attached to a sterilization container for containing the endoscope during a sterilization procedure, the sterilization container being sealable, gas transmissive and microbe impervious.

The present invention also comprises a method for equalizing the pressure within an interior space of an endoscope with a pressure in an environment about the endoscope. The method comprises the following steps. When the pressure in the interior space exceeds the pressure in the environment by more than a predetermined value, open a port between the interior space and the environment to equalize the pressure therebetween. When the pressure within the interior space is equalized with the pressure in the environment, block the port to inhibit flow of gas or other matter from the environment into the interior space through the port.

When the gas in the environment contains a known agent, it is preferably filtered as it enters the port from the environment to neutralize the agent. When the agent comprises hydrogen peroxide, it is preferably neutralized with a catalyst, such as copper, which decomposes the hydrogen peroxide into water and oxygen.

The method is most preferably employed in conjunction with a sterilization procedure in which the endoscope is placed into a sterilization chamber, the pressure is lowered below atmospheric pressure, an antimicrobial gas is introduced into the sterilization chamber, the gas is scavenged from the sterilization chamber and the pressure within the sterilization chamber is returned to atmospheric pressure.

BRIEF DESCRIPTION OF THE DRAWINGS

FIG. 5 is a diagrammatical view of the device of FIG. 3 in place upon an endoscope and which is further attached to a sterilization container shown in block diagram form.

DETAILED DESCRIPTION

Figure 1:
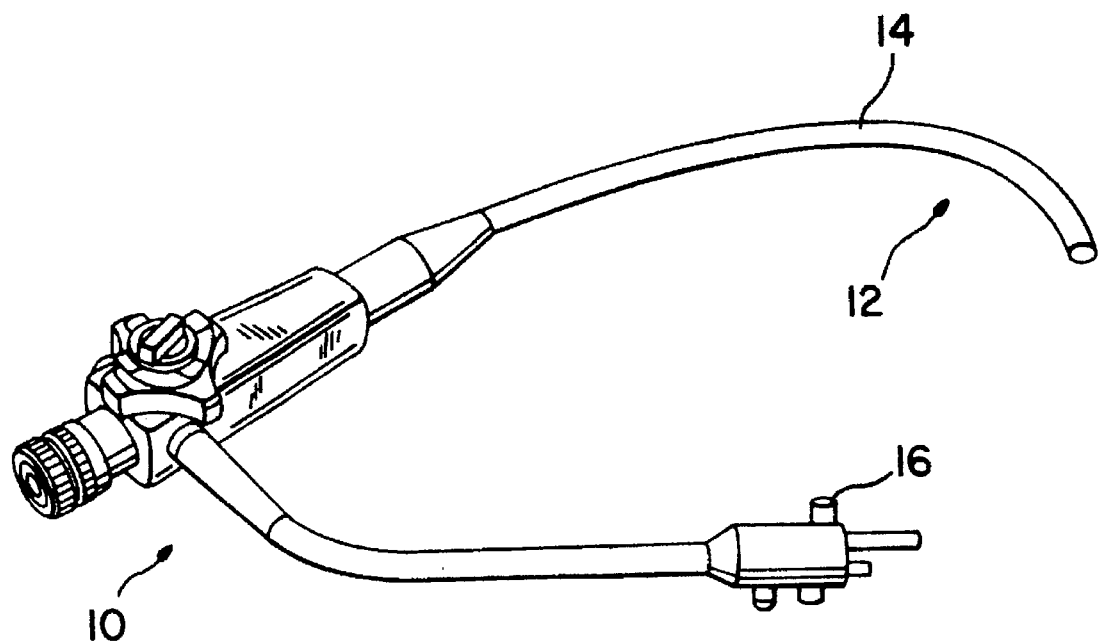
FIG. 1 is a perspective view of an endoscope of the general type for which the device and method according to the present invention are adapted.

Referring now to FIG. 1, a typical endoscope 10 comprises a flexible potion 12 for insertion into a body with the flexible portion being encased within an elastomeric sheath 14. A port 16 opens to an interior space (not shown) of the endoscope 10 and allows pressure communication between the interior space and the environment about the endoscope 10.

Figure 2:
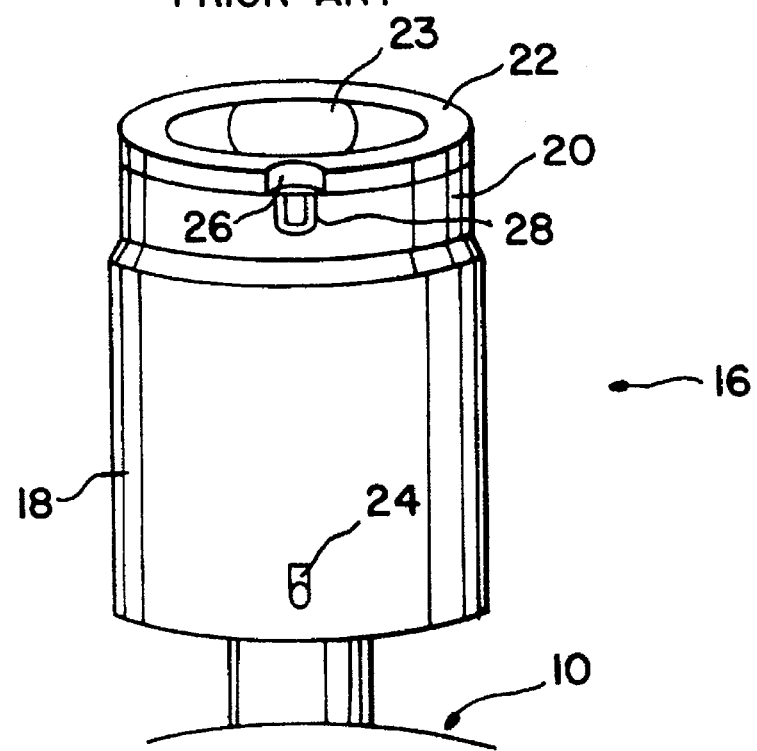
FIG. 2 is a perspective view of a pressure port of the endoscope of FIG. 1.

Turning to FIG. 2, the port 16 comprises a cylindrical body 18 projecting outwardly from the endoscope 10. An annular rotatable collar 20 is received within the port body 18 and an annular cover plate 22 disposed above the collar 20 rigidly connects to the body 18. Rotation of the collar 20 operates a valve member 23 to selectively open and close the interior of the endoscope 10 to atmosphere through the port 16.

A guide pin 24 projects radially from the port body 18 and a notch 26 on the cover plate 22 aligns with a notch 28 on the collar 20 so that a pin (not shown in FIG. 2) may travel axially into the collar notch 28 for rotation of the collar 20. The port 16 is adapted to receive at least two devices. The first, a sterilization cap (not shown) has a track for receiving the guide pin 24 and an engagement pin for engaging the collar notch 28. When the cap is placed onto the port 16 and rotated, the valve member 23 opens to place the interior of the endoscope 10 into pressure communication with the atmosphere through a hole in the cap. The port 16 is also adapted to receive a leakage detector, such as disclosed by the Shimizu U.S. Pat. No. 4,506,544, issued Mar. 26, 1985 and incorporated herein by reference.

Figure 3:
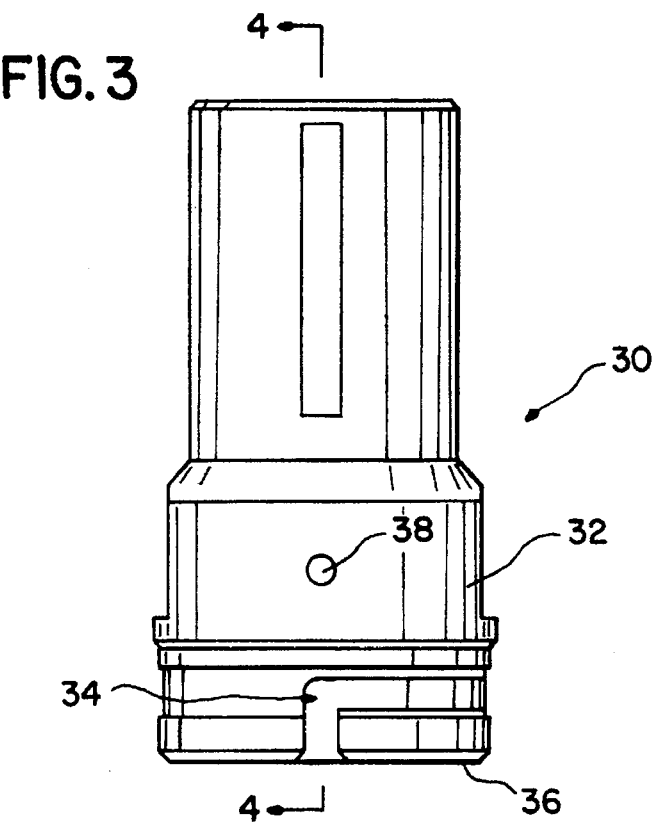
FIG. 3 is an elevation view of a device according to the present invention.

FIG. 3 illustrates an improved sterilization cap 30 according to the present invention. The cap 30 comprises a generally cylindrical body 32 which has a channel 34 therein for receiving the guide pin 24 on the port 16 (see FIG. 2). The channel 34 extends axially into the body 32 a short distance from a body first end 36 from whence it extends one quarter of the circumference of the body 32. Accordingly, the cap 30 may be placed over the port 16, with the pin 24 received within the channel 34, and the cap 30 then rotated one quarter turn as the guide pin 24 travels along the channel 34. An engagement pin 38 extends radially inwardly from the body 32 and engages the collar notch 28 when the guide pin 24 is received within the channel 34 and thereby forms an opening means for opening the valve member 23. As the cap 30 is rotated, the engagement pin 38 rotates the collar 20 to open the valve member 23.

Figure 4:
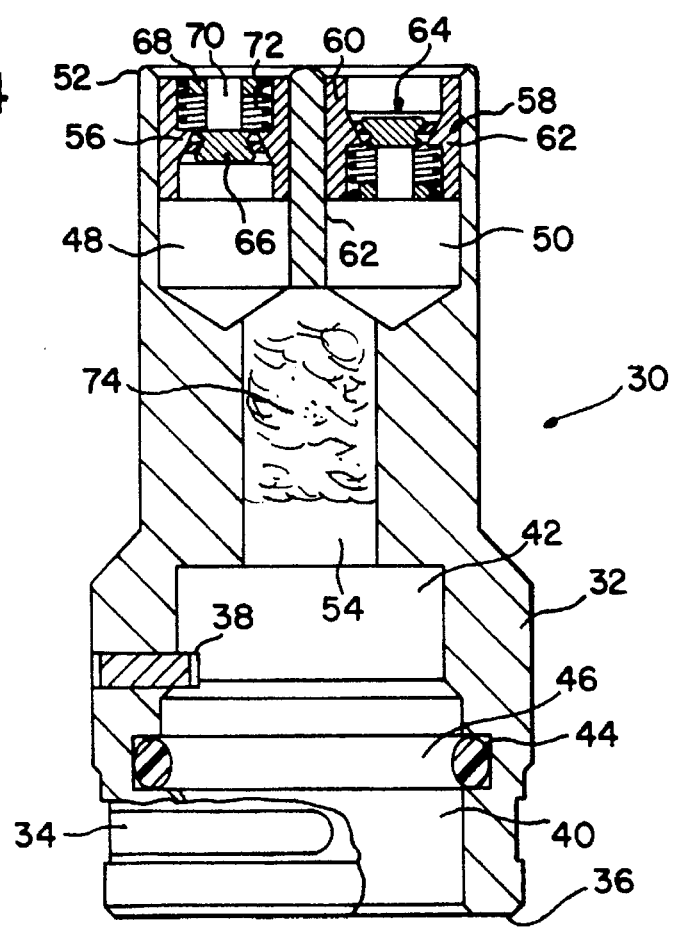
FIG. 4 is a partial sectional view taken along lines 4—4 of FIG. 3.

FIG. 4 shows the interior structure of the cap 30 and discloses a first axial bore 40 extending into the body 32 from the first end 36 and sized to receive the port body 18 (see FIG. 2). A second axial bore 42 extends somewhat further into the cap body 32 and has a smaller diameter so as to receive the port collar 20 and cover plate 22. An annular groove 44 in the body 32 at the first bore 40 receives an O-ring 46 to seal the cap 30 to the port 16.

An inlet valve bore 48 and an outlet valve bore 50 extend axially into the valve body 32 in side-by-side relationship from a second end 52 thereof. A header 54 extends from the second axial bore 42 to both of the inlet and outlet valve bores 48 and 50 to place them into fluid communication with the second axial bore 42. An inlet check valve 56 and an outlet check valve 58 are disposed respectively in the inlet and outlet valve bores 48 and 50. Each of the inlet and outlet check valves 56 and 58 allow only unidirectional flow, and only in response to a predetermined pressure gradient. Similar check valves are described in the Winn U.S. Pat. No. 4,129,145 issued Dec. 12, 1978 and incorporated herein by reference.

In general, each of the inlet and outlet check valves 56 and 58 comprises a tubular valve body 60 having an interior annular valve seat 62. A poppet 64 disposed within the valve body 60 comprises: a discoidal valve member 66 downstream of the valve seat 62, a discoidal spring seat 68 upstream of the valve seat 62, and a shaft 70 which passes through the valve seat 62 and connects the valve member 66 and spring seat 68. A spring 72 extends between the valve seat 62 and the spring seat 68 to bias the valve member 66 against the valve seat 62 and thereby form a positive closure means. When pressure against the valve member 66 overcomes the force of the spring, the valve member 66 lifts off of the valve seat 62 to allow flow through the valve body 60.

The check valves 56 and 58 allow the pressure to equalize between the interior of the endoscope 10 and the environment surrounding the endoscope sheath 14, while preventing free flow of gas into the endoscope 10. As used herein, the pressure is considered equalized when the pressure differential across the sheath 14 is below a predetermined value such that the sheath is protected and including a prudent safety margin. The springs 72 determine the pressure necessary to open the check valves 56 and 58. Preferably, the spring force should require a pressure differential of 1.5 to 5 pounds per square inch to operate the check valves. A check valve with no biasing, such as a simple swing check valve, could substitute for either or both of the check valves 56 and 58. However, the slight biasing force provided by the springs 72 keeps the check valves 56 and 58 closed when the pressure is equalized to further prevent antimicrobial gas from entering the endoscope during the sterilization cycle.

The sterilization cap 30 is particularly useful with vapor phase hydrogen peroxide sterilization, either alone or in connection with a plasma field, such as disclosed in the Jacobs et al. U.S. Pat. No. 4,643,876 issued Feb. 17, 1987 and incorporated herein by reference. To further ensure that hydrogen peroxide from the sterilization cycle does not reach the inside of the endoscope 10, a filter media 74 may be provided in the inlet valve chamber 48 or more preferably in the header 54. The filter 74 preferably comprises a material capable of acting as a catalyst to decompose the hydrogen peroxide into harmless water and oxygen. Copper, silver, iron, platinum and their alloys are among the metals which act as a catalyst against hydrogen peroxide. Copper wool has been found to be particularly suitable as a filter material.

Other means may be provided for preventing a residual anti-microbial agent from entering the endoscope 10, at least in a harmful form. For hydrogen peroxide anti-microbials, other catalysts such as catalase or chemical reactants may be provided to decompose or otherwise render harmless any residual hydrogen peroxide. Further, an absorbent, such as cellulosic material, may be provided in addition to or in place of the copper filter 74 to absorb residual hydrogen peroxide and prevent it from entering the endoscope 10. Alternatively, a filtration membrane may be provided for allowing the passage of air but blocking the passage of hydrogen peroxide.

While these techniques are particularly useful for eliminating residual hydrogen peroxide, they also may eliminate residual amounts of other anti-microbial agents used in similar sterilization cycles. Catalysts, reactive chemical agents, absorbents, physical filters such as filtration membranes or other means may be used to prevent active anti-microbial agent from entering the endoscope while allowing air to pass into and out of the endoscope. For instance, in the case of an acidic or basic anti-microbial agent, an appropriate substance may be added to neutralize the pH into a harmless range.

Typically, instruments are placed into a vapor transmissive, microbe filtering wrap or container (not shown) prior to sterilization. One typical device is disclosed in the Nichols U.S. Pat. No. 4,716,025 issued Dec. 29, 1987 and incorporated herein by reference. After the sterilization procedure is complete, the instruments may be left inside of the wrap or container until ready for use, thus maintaining their sterility. Often specialized containers are provided for instruments such as endoscopes. To promote operator compliance in using the cap 30, it could be attached to such a specialized container whereby the operator would be reminded to employ the cap 30 during sterilization by the cap's presence in the container.

FIG. 5 illustrates, in block diagram form, such a container 76 for containing the endoscope 10. A connecting member 78 leads between the container 76 and the cap 30 so that the presence of the cap 30 will remind an operator to attach the cap to the endoscope port 16 prior to a sterilization procedure.

To sterilize the endoscope 10 in a low pressure gaseous antimicrobial atmosphere, the sterilization cap 30 is first placed onto the port 16 of the endoscope 10. The guide pin 24 enters the channel 34 on the cap 30 to guide the movement of the cap 30 onto the port 16. The cap 30 is first pushed axially onto the port and then rotated one quarter turn. As the guide cap 30 is pushed axially onto the port 16, the engagement pin 38 travels through the notch 26 in the cover plate 22 and enters the notch 28 in the collar 20. As the cap 30 is rotated through one quarter turn, the collar 20 rotates to place the valve member 23 into the open position, thereby placing the interior of the endoscope into fluid communication with the second axial bore 42 of the cap 30.

Typically, pressure is reduced during such a sterilization cycle prior to application of the antimicrobial agent. As the pressure is reduced, the outlet check valve 58 opens to allow air within the endoscope to escape and protect the integrity of the elastomeric sheath 14. As the pressure in the endoscope 10 equalizes with its surrounding atmosphere, the outlet check valve closes and seals the interior of the endoscope from the sterilizing atmosphere. When used with a hydrogen peroxide antimicrobial agent, the filter media 74 neutralizes any of the hydrogen peroxide which may happen to leak past the inlet or outlet check valves 56 and 58.

At the end of the sterilization cycle, the antimicrobial agent is scavenged from the environment surrounding the endoscope 10. Typically, the sterilization occurs within a sealed chamber, and when performed in connection with electromagnetic radiation to produce a plasma field, the hydrogen peroxide is converted to water and oxygen during the sterilization cycle. However, in the absence of a plasma field, the hydrogen peroxide is typically vented from the chamber. In any event, at some point after the sterilization is complete, the pressure is raised within the sterilization chamber (not shown). At a predetermined pressure gradient, the inlet check valve 56 opens to allow air within the sterilization chamber to enter the endoscope. If there is residual hydrogen peroxide within the sterilization chamber, the filter media 74 will neutralize it before it enters the pert 16. After the sterilization cycle is complete, the sterilization cap should be removed from the endoscope 10.

While the invention has been described with regard to a particular embodiment thereof, those skilled in the art will understand, of course, that the invention is not limited thereto since modifications can be made by those skilled in the art, particularly in light of the foregoing teachings. Reasonable variation and modification are possible within the foregoing disclosure of the invention without the departing from the spirit of the invention. For instance, the cap 30 would be quite useful with only the outlet check valve 58 and without the inlet check valve 56. Sufficient structure underlies the sheath 14 in most endoscopes such that low pressures within the endoscope 10 will not likely damage the sheath 14. Also, it should be understood that the present invention, including the chemical agent filtration aspects, is useful in protecting instruments not only during hydrogen peroxide based sterilization but also during sterilization with other agents, including peracetic acid, which may possibly harm the interior of an instrument such as an endoscope.

What is claimed is:

1. A pressure equalization device for equalizing the pressure within an endoscope having a port to an internal space thereof from an environment thereabout, the device comprising:

connection means for connecting the device to the endoscope port;

an outlet check valve in fluid communication between the environment and the endoscope port when the connection means is connected to the endoscope port, the outlet check valve being oriented to allow flow out of the port into the environment and inhibit flow into the port from the environment; and an outlet flow path from the port to the environment through the outlet check valve and a chemical inactivation filter means in the outlet flow path for inactivating a chemical agent in the environment thereabout and thereby preventing the chemical agent from entering the port in an active form, whereby when the endoscope is subjected to a reduced pressure in the environment, gas within the endoscope interior space may escape to the environment through the outlet check valve to relieve pressure within the interior space, and whereby, after the pressure in the interior space is equalized with the pressure in the environment, the outlet check valve inhibits reverse flow therethrough of gas from the environment into the interior space.

2. A device according to claim 1 wherein the filter means comprises a catalyst for decomposing hydrogen peroxide into water and oxygen.

3. A device according to claim 2 wherein the catalyst comprises copper, platinum, silver, iron or an alloy thereof.

4. A pressure equalization device according to claim 1 and further comprising:
an inlet check valve means in fluid communication between the environment and the endoscope port when the connection means is connected thereto; wherein the inlet check valve means allows flow therethrough into the port only in response to a downstream pressure gradient exceeding a first predetermined value.

5. A device according to claim 4 and further comprising an inlet flow path through the inlet check valve into the port and a filter means in the inlet flow path for preventing a chemical agent from entering the port in an active form.

6. A device according to claim 5 wherein the filter means comprises a catalyst for decomposing hydrogen peroxide into water and oxygen.

7. A device according to claim 4 wherein the predetermined value is in the range of 1.5 to 5 pounds per square inch.

8. A device according to claim 4 wherein the outlet check valve further comprises a positive closure means whereby the outlet check valve is closed to all flow except in response to a downstream pressure gradient exceeding a second predetermined value.

9. A device according to claim 1 wherein the outlet check valve further comprises a positive closure means whereby the outlet check valve is closed to all flow except in response to a downstream pressure gradient exceeding a predetermined value.

10. A pressure equalization device according to claim 9 wherein the predetermined value is in the range of 1.5 to 5 pounds per square inch.

11. A device according to claim 1 and further comprising opening means associated with said connection means for opening a valve member in the port when the connection means is connected thereto.

12. A pressure equalization system for equalizing the pressure within an endoscope having a port to an internal space thereof from an environment thereabout, the system comprising:
a sterilization cap comprising:
connection means for connecting the device to the endoscope port;
an outlet check valve in communication between the environment and the endoscope port when the connection means is connected to the endoscope port, the outlet check valve being oriented to allow flow out of the port into the environment and inhibit flow into the port from the environment; and
a sterilization container for containing the endoscope during a sterilization procedure, the sterilization container being sealable, gas transmissive and microbe impervious, the sterilization cap being connected to the sterilization container whereby its presence may remind a user to employ the sterilization cap during a sterilization procedure.

13. A system according to claim 15, the sterilization cap and further comprising an outlet flow path from the port to the environment through the outlet check valve and a chemical inactivation filter means in the outlet flow path for inactivating a chemical agent in the environment thereabout and thereby preventing the chemical agent from entering the port in an active form.

14. A system according to claim 16 wherein the filter means comprises a catalyst for decomposing hydrogen peroxide into water and oxygen.

15. A system according to claim 17 wherein the catalyst comprises copper, platinum, silver, iron or an alloy thereof.

16. A system according to claim 18 wherein the catalyst comprises copper wool.

17. A pressure equalization device for equalizing the pressure within an endoscope having a port to an internal space thereof from an environment thereabout, the device comprising:
connection means for connecting the device to the endoscope port;
an outlet check valve in fluid communication between the environment and the endoscope port when the connection means is connected to the endoscope port, the outlet check valve being oriented to allow flow out of the port into the environment and inhibit flow into the port from the environment; and
an outlet flow path from the port to the environment through the outlet check valve and a chemical inactivation filter means in the outlet flow path for inactivating a chemical agent in the environment thereabout and thereby preventing the chemical agent from entering the port in an active form and wherein the filter means comprises copper wool for catalytically decomposing hydrogen peroxide into water and oxygen,
whereby when the endoscope is subjected to a reduced pressure in the environment, gas within the endoscope interior space may escape to the environment through the outlet check valve to relieve pressure within the interior space, and whereby, after the pressure in the interior space is equalized with the pressure in the environment, the outlet check valve inhibits reverse flow therethrough of gas from the environment into the interior space.

18. A pressure equalization device for equalizing the pressure within an endoscope having a port to an internal space thereof from an environment thereabout, the device comprising:
connection means for connecting the device to the endoscope port;
an outlet check valve in fluid communication between the environment and the endoscope port when the connection means is connected to the endoscope port, the outlet check valve being oriented to allow flow out of the port to the environment and inhibit flow into the port from the environment;
an inlet check valve means in fluid communication between the environment and the endoscope port when the connection means is connected thereto; wherein the inlet check valve means allows flow therethrough into the port only in response to a downstream pressure gradient exceeding a first predetermined value; and an inlet flow path from the environment to the port through the inlet check valve and a chemical inactivation filter means in the inlet flow path for inactivating a chemical agent in the environment thereabout and thereby preventing the chemical agent from entering the port in an active form, and wherein the chemical inactivation means comprises copper wool for catalytically decomposing hydrogen peroxide into water and oxygen, whereby when the endoscope is subjected to a reduced pressure in the environment, gas within the endoscope interior space may escape to the environment through the outlet check valve to relieve pressure within the interior space, and whereby, after the pressure in the interior space is equalized with the pressure in the environment, the outlet check valve inhibits reverse flow therethrough of gas from the environment into the interior space.

* * * * *